United States Patent [19]

Albright et al.

[11] Patent Number: 4,654,343

[45] Date of Patent: Mar. 31, 1987

[54] N-SUBSTITUTED-N[3-(1,2,4-TRIAZOLO[4,3-B]PYRIDAZIN-6-YL)PHENYL]ALKANAMIDES, CARBAMATES AND UREAS

[75] Inventors: Jay D. Albright, Nanuet, N.Y.; Dennis W. Powell, Greenwich, Conn.; John P. Dusza, Nanuet, N.Y.

[73] Assignee: American Cyanamid Company, Stamford, Conn.

[21] Appl. No.: 793,437

[22] Filed: Oct. 31, 1985

[51] Int. Cl.[4] .................. A61K 31/50; C07D 471/02; C07D 237/12; C07D 237/14
[52] U.S. Cl. .................................. 514/248; 544/224; 544/236; 544/239
[58] Field of Search .................... 544/236; 514/248

[56] References Cited

U.S. PATENT DOCUMENTS

| 4,112,095 | 9/1978 | Allen, Jr. et al. | 514/248 |
| 4,117,130 | 9/1978 | Allen, Jr. et al. | 514/248 |
| 4,230,705 | 10/1980 | Allen, Jr. et al. | 544/236 |
| 4,260,755 | 4/1981 | Moran et al. | 544/236 |

OTHER PUBLICATIONS

Albright et al., J. Med. Chem., vol. 24, pp. 592–600, 1981.

Primary Examiner—Donald G. Daus
Assistant Examiner—Stephen M. Kapner
Attorney, Agent, or Firm—Susan H. Rauch

[57] ABSTRACT

Novel organic compounds which are N-substituted-N-[3-(1,2,4-triazolo[4,3-b]pyridazin-6-yl)phenyl]alkanamides, carbamates and ureas which are useful as anxiolytic or antiepileptic agents, methods of using the compounds, compositions of matter containing them as the active ingredient and processes for their production.

15 Claims, No Drawings

N-SUBSTITUTED-N[3-(1,2,4-TRIAZOLO[4,3-B]PYRIDAZIN-6-YL)PHENYL]ALKANAMIDES, CARBAMATES AND UREAS

SUMMARY OF THE INVENTION

This invention relates to new organic compounds which are N-substituted-N-[3-(1,2,4-triazolo[4,3-b]pyridazin-6-yl)phenyl]alkanamides, carbamates and ureas which are useful as anxiolytic or antiepileptic agents as well as sedative-hypnotic and skeletal muscle relaxant agents. This invention also relates to the methods of using the novel compounds, to compositions of matter containing them as the active ingredient and to processes for their production.

DETAILED DESCRIPTION OF THE INVENTION

The novel compounds of this invention are represented by the following structural formula:

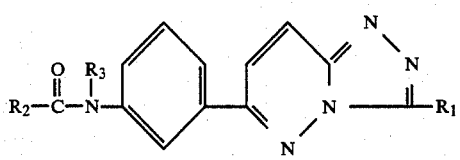

Formula 1 wherein $R_1$ is selected from the group consisting of hydrogen, alkyl($C_1$–$C_3$), amino, monoalkyl($C_1$–$C_3$)amino, dialkyl($C_1$–$C_3$)amino, —NHCOalkyl($C_1$–$C_3$) and N-alkyl($C_1$–$C_3$)—CO-alkyl($C_1$–$C_3$); $R_2$ is selected from the group consisting of hydrogen, alkyl($C_1$–$C_6$), cycloalkyl($C_3$–$C_6$), —O-alkyl($C_1$–$C_6$), —NH-alkyl(-$C_1$–$C_3$), —N-dialkyl($C_1$–$C_3$), —$(CH_2)_n$—O-alkyl(-$C_1$–$C_3$), —$(CH_2)_n$—NH-alkyl($C_1$–$C_3$) and —$(CH_2)_n$—N-dialkyl($C_1$–$C_3$), where n is an integer from 1 to 3 inclusive; and $R_3$ is selected from the group consisting of alkyl($C_1$–$C_6$), alkenyl($C_2$–$C_6$), —$CH_2C\equiv CH$, cycloalkyl($C_3$–$C_6$)methyl, —$CH_2OCH_3$ and —$CH_2CH_2OCH_3$. Preferably $R_1$ is alkyl ($C_1$–$C_3$), $R_2$ is alkyl(-$C_1$–$C_6$) and $R_3$ is alkyl ($C_1$–$C_6$). Most preferably, $R_1$ is methyl, $R_2$ is alkyl ($C_1$–$C_3$) and $R_3$ is alkyl($C_1$–$C_2$).

The novel compounds of Formula 1, where $R_2$ and $R_3$ are as previously defined and $R_1$ is hydrogen or alkyl($C_1$–$C_3$) may be prepared as shown in Scheme I.

Scheme I

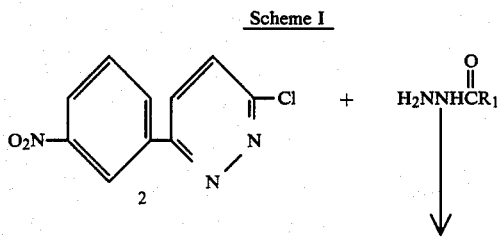

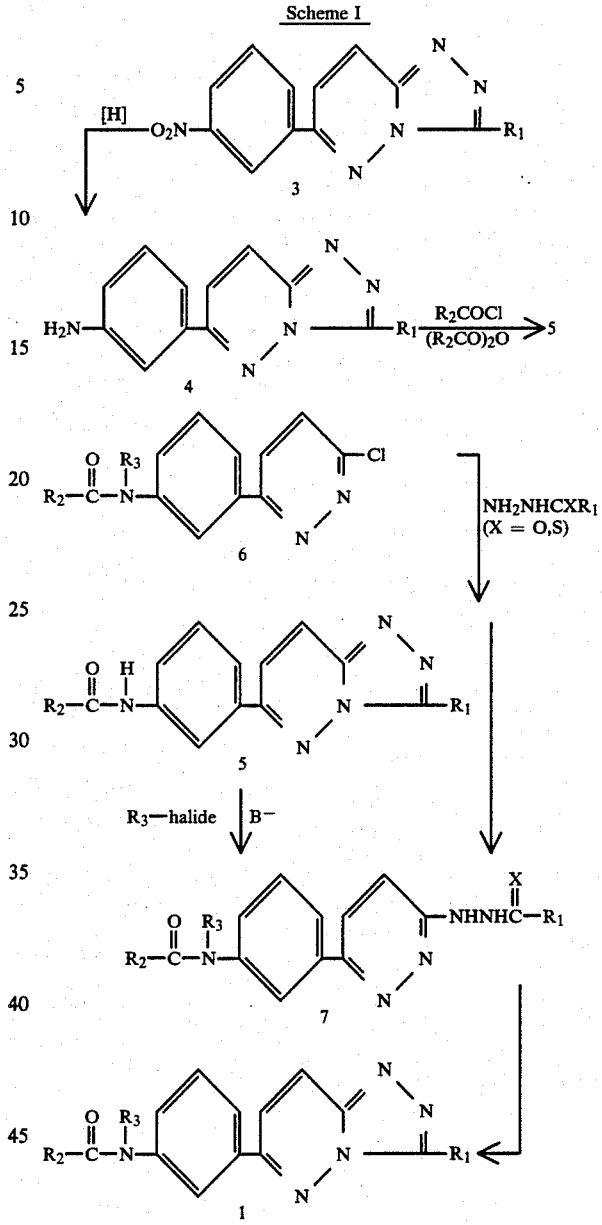

In accordance with Scheme I, which is the preferred method of preparation, the 3-chloro-6-(3-nitrophenyl)-pyridiazine 2 is reacted with formylhydrazide ($R_1$=H) or an alkanoylhydrazine [$R_1$=alkyl($C_1$–$C_3$)] in refluxing n-butanol, giving a 6-(3-nitrophenyl)-1,2,4triazolo[4,3-b]pyridazine 3, as described by J. D. Albright, et. al., J. Med. Chem., 24, 592 (1981).

The nitro group may be reduced under standard conditions for conversion of nitro groups to amino groups as described in Tetrahedron Letters, 25, 839 (1984) or 25, 3415 (1984); or under standard catalytic reduction with 10% palladium on carbon under 10–40 lbs of hydrogen pressure in an appropriate solvent such as trifluoroacetic acid.

The resulting 6-(3-aminophenyl)-1,2,4-triazolo[4,3-b]pyridazine 4 is reacted with an $R_2$ carbonyl chloride, alkanoic acid anhydride or dialkyl dicarbonate to give the intermediate 5 which is then reacted with an $R_3$ halide in the presence of a base such as sodium hydride, giving the compounds 1 of this invention, where $R_1$ is hydrogen or alkyl($C_1$-$C_3$) and $R_2$ and $R_3$ are as previously defined.

Alternatively, but less preferably, the compounds of formula 1, where $R_1$, $R_2$ and $R_3$ are as previously defined, may be prepared by reaction of the intermediates N-[3-(6-chloro-3-pyridazinyl)phenyl]alkanamides of formula 6 with formylhydrazide, alkanoylhydrazines, thiosemicarbazide, 4-alkyl-3-thiosemicarbazides or 4-dialkyl-3-thiosemicarbazides in an appropriate solvent such as ethanol, n-butanol and the like. The preparation of the intermediates of formula 6 is described in Scheme II below.

In lower boiling solvents such as ethanol, the open chain derivatives 7 are generally formed. These derivatives are then cyclized by heating in a higher boiling solvent or by heating in acetic acid, or by heating in the presence of Lewis acids in an inert solvent. In the cases where the 3-chloropyridazine intermediates 6 are reacted with 3-thiosemicarbazides, the preferred method is reaction in a lower boiling solvent such as ethanol, isolation of the intermediate 7 (X=S; $R_1$=NH$_2$) and cyclization in glacial acetic acid to give compounds of formula 1 where $R_1$ is amino.

The intermediate N-[3-(6-chloro-3-pyridazinyl)-phenyl]alkanamides 6 are prepared according to reaction Scheme II.

chloropyridazines 11 are prepared by reacting 10 with phosphorus oxychloride. Introduction of an $R_3$ substitutent on the nitrogen of the HNCOR$_2$ group in the derivatives 11 may be carried out by first forming the anion of the HNCOR$_2$ group with sodium hydride, followed by reaction of the anion thus formed with an $R_3$-halide, wherein $R_3$ is as previously defined.

Derivatives of formula 1 wherein $R_1$ is hydrogen or alkyl($C_1$-$C_3$) may be prepared according to Scheme III.

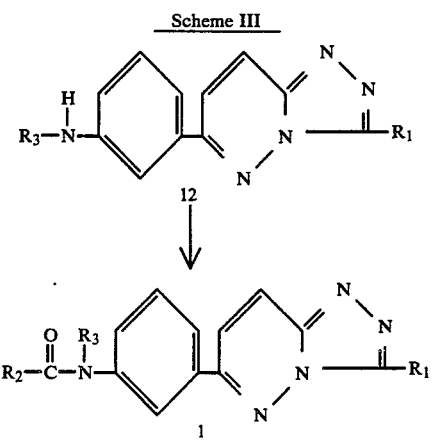

Scheme III

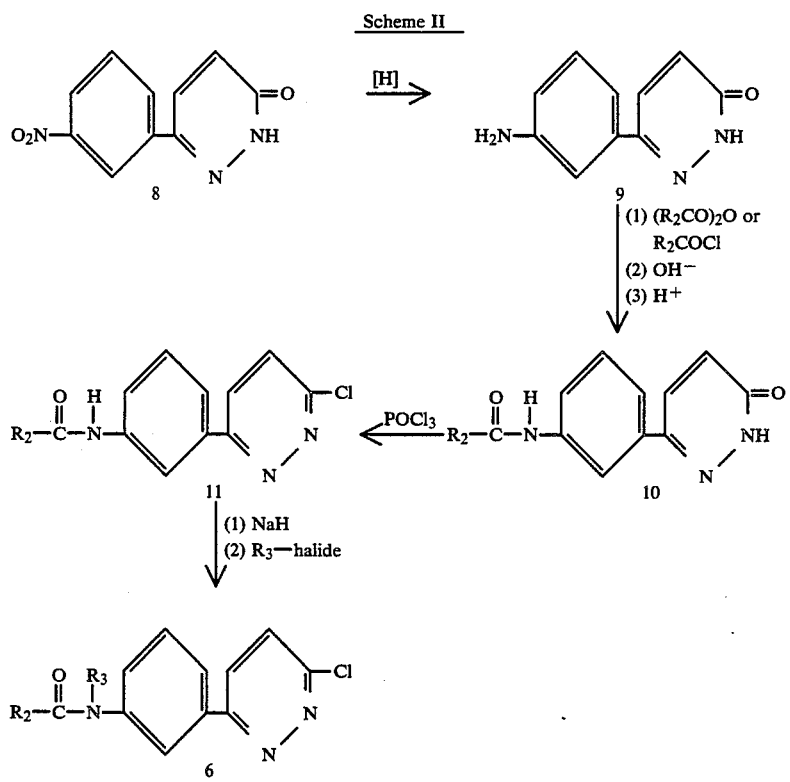

Scheme II

In accordance with Scheme II the 6-(3-nitrophenyl)-3(2H)pyridazinone 8 is reduced under chemical reduction conditions or under catalytic reduction conditions (10% palladium on carbon) to give the 6-(3-aminophenyl)-3(2H)-pyridazinone 9. Reaction of 9 with lower alkyl($C_1$-$C_6$) acid chlorides or preferably lower alkyl(-$C_1$-$C_6$) acid anhydrides affords the N-alkanoyl derivatives 10 wherein $R_2$ is alkyl($C_1$-$C_6$). Reaction of 9 with alkyl($C_1$-$C_6$)chloroformates affords derivatives 10 wherein $R_2$ is O-alkyl($C_1$-$C_6$). The intermediate 6-

In accordance with Scheme III the intermediate 6-[3-(N-alkylamino)phenyl]-1,2,4-triazolo[4,3-b]pyridazine 12 is reacted with an alkyl isocyanate, alkanoic acid chloride, alkyl chloroformate, dialkyl carbamoyl chloride, alkanoic acid anhydride or dialkyl dicarbonate to give the products 1, wherein $R_1$ is hydrogen or alkyl($C_1$-$C_3$).

Alternatively the nitro group in 3-chloro-6-(3-nitrophenyl)pyridazine 2 is reduced to give the 3-chloro-6-(3-aminophenyl)pyridazine 13 which may be converted to the products ($R_1$=H, alkyl) of this invention as shown in Scheme IV.

Psychotropic Drugs" in An Introduction to Psychopharmacology, Eds. R. R. Rech and K. E. Moore, Raven Press, New York, pp 237–288 (1971)] that there is a high degree of correlation between antagonism of pentylenetetrazole seizures in rats and antianxiety and anticonvulsant effects in higher warm-blooded animals. The results of this test on representative compounds of

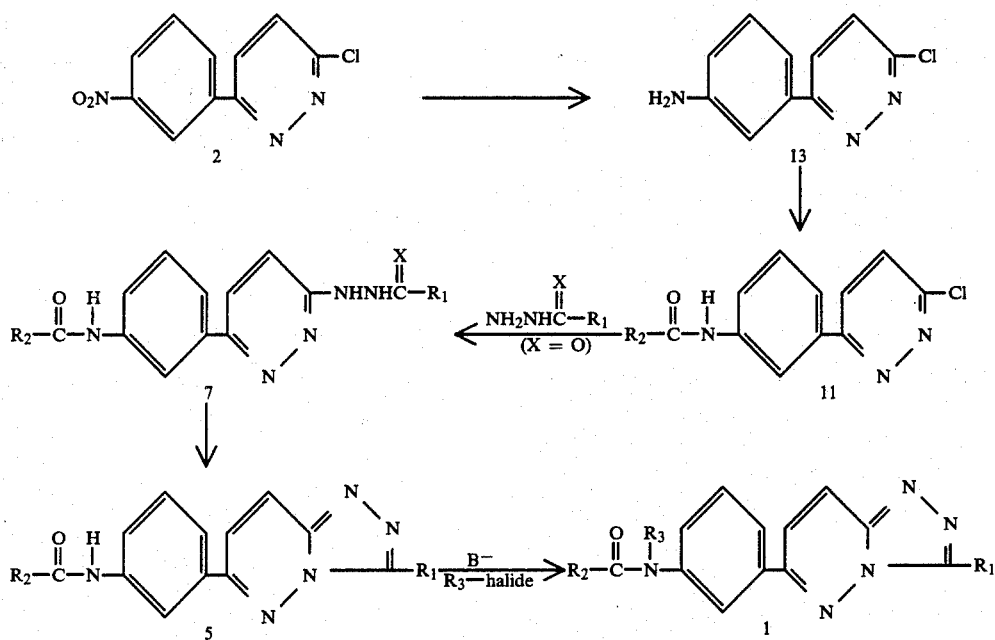

Scheme IV

In accordance with Scheme IV, reaction of 13 with alkanoic acid chlorides, alkanoic acid anhydrides, dialkyl dicarbonates, alkyl chloroformates, alkyl isocyanates or dialkylcarbamoyl chlorides affords the alkanamide carbamate and urea derivatives 5. Introduction of the $R_3$ substituent is then carried out under N-alkylating conditions in the presence of a base such as sodium hydride.

The novel compounds of the present invention possess central nervous system activity at nontoxic doses and as such are useful as anxiolytic agents. That is, they produce certain responses in standard tests with laboratory animals which are known to correlate well with relief of anxiety in man. Furthermore, these compounds have been shown by biological data to be useful as antiepileptic agents, particularly in the treatment of grand mal seizures, and also as sedative-hypnotic and skeletal muscle relaxant agents.

The antianxiety and anticonvulsant properties of the novel compounds of the present invention were established in a test which indicates both anxiolytic and antiepileptic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has been reported [R. T. Hill and D. H. Tedeschi, "Animal Testing and Screening Procedures in Evaluating this invention are shown in Table I.

TABLE I

| Protection Against Clonic Seizures Caused by Pentylenetetrazole in Rats | | |
|---|---|---|
| Compound | Dose (mg/kg) | % of Rats Protected |
| N—Ethyl-N—[3-(3-methyl-1,2,4-triazolo[4,3-b]pyridazin-6-yl)phenyl]acetamide | 12.5 | 100 |
| N—Methyl-N—[3-(3-methyl-1,2,4-triazolo[4,3-b]pyridazin-6-yl)phenyl]acetamide | 6.0 | 100 |
| N—Methyl-N—[3-(3-methyl-1,2,4-triazolo[4,3-b]pyridazin-6-yl)phenyl]propanamide | 12.5 | 25 |
| N—Ethyl-N—[3-(3-methyl-1,2,4-triazolo[4,3-b]pyridazin-6-yl)phenyl]propanamide | 3.1 | 75 |
| Ethyl-[3-(3-methyl-1,2,4-triazolo[4,3-b]pyridazin-6-yl)phenyl]carbamic acid, methyl ester | 3.1 | 75 |
| Methyl[3-(3-methyl-1,2,4-triazolo[4,3-b]pyridazin-6-yl)phenyl]carbamic acid, methyl ester | 25 | 100 |
| N—Ethyl-N,N'dimethyl-N—[(3-methyl-1,2,4-triazolo[4,3-b]pyridazin-6-yl)phenyl]urea | 12.5 | 75 |
| N,N,N'—Trimethyl-N'—[3-(3-methyl-1,2,4-triazolo[4,3-b]pyridazin-6-yl)phenyl]urea | 25 | 50 |
| N—Methyl-N—[3-(1,2,4-triazolo[4,3-b]pyridazin-6-yl)phenyl]acetamide | 25 | 50 |
| N—Ethyl-N—[3-(1,2,4-triazolo[4,3-b]pyridazin-6-yl)phenyl]acetamide | 25 | 100 |
| N—Methyl-N—[3-(1,2,4-triazolo[4,3-b]pyridazin-6-yl)phenyl]propanamide | 25 | 100 |
| N—Ethyl-N—[3-(1,2,4-triazolo[4,3-b]pyridazin-6-yl)phenyl]propanamide | 3.1 | 50 |
| Ethyl-[3-(1,2,4-triazolo[4,3-b]- | 25 | 100 |

TABLE I-continued
Protection Against Clonic Seizures Caused by Pentylenetetrazole in Rats

| Compound | Dose (mg/kg) | % of Rats Protected |
|---|---|---|
| pyridazin-6-yl)phenyl]carbamic acid, methyl ester | | |
| Methyl[3-(1,2,4-triazolo[4,3-b]-pyridazin-6-yl)phenyl]carbamic acid, methyl ester | 25 | 25 |
| N—[3-(3-Methyl-1,2,4-triazolo[4,3-b]-pyridazin-6-yl)phenyl-N—2-propenyl-acetamide | 6.25 | 100 |
| N—(Cyclopropylmethyl)-N—[3-(3-methyl-1,2,4-triazolo[4,3-b]pyridazin-6-yl)-phenyl]acetamide | 12.5 | 75 |
| N—[3-(3-Methyl-1,2,4-triazolo[4,3-b]-pyridazin-6-yl)phenyl]-N—2-propynyl-acetamide | 3.1 | 100 |

Another test which has been used to assess antianxiety effects is a non-conditioned passive avoidance procedure described by J. R. Vogel, B. Beer and D. E. Clody, "A Simple and Reliable Conflict Procedure for Testing Anti-anxiety Agents", Psychopharmacologia, 21, 1–7 (1971). A conflict situation is induced in rats by a modification of this method.

Groups of 6 naive, Wistar strain rats, weighing 200–240 g each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 or 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group. The test compounds are considered active if the number of shocks received by the test group is significantly higher than the control group by the Mann-Witney U test. Results of this test on representative compounds of this invention appear in Table II.

TABLE II
Nonconditioned Passive Avoidance Test in Rats

| Compound | Dose (mg/kg) | Results |
|---|---|---|
| N—Ethyl-N—[3-(3-methyl-1,2,4-triazolo[4,3-b]pyridazin-6-yl)phenyl]acetamide | 0.8 | Active |
| N—Methyl-N—[3-(3-methyl-1,2,4-triazolo[4,3-b]pyridazin-6-yl)phenyl]acetamide | 3.1 | Active |
| N—Methyl-N—[3-(3-methyl-1,2,4-triazolo[4,3-b]pyridazin-6-yl)phenyl]propanamide | 3.1 | Active |
| N—Ethyl-N—[3-(3-methyl-1,2,4-triazolo[4,3-b]pyridazin-6-yl)phenyl]propanamide | 3.1 | Active |
| Ethyl-[3-(3-methyl-1,2,4-triazolo[4,3-b]pyridazin-6-yl)phenyl]carbamic acid, methyl ester | 1.5 | Active |
| [3-(3-Methyl-1,2,4-triazolo[4,3,-b]-pyridazin-6-yl)phenyl]carbamic acid, methyl ester | 25 | Active |
| Methyl[3-(3-methyl-1,2,4-triazolo[4,3-b]pyridazin-6-yl)phenyl]carbamic acid, methyl ester | 3.1 | Active |
| N—Ethyl-N',N'—dimethyl-N—[(3-methyl-1,2,4-triazolo[4,3-b]pyridazin-6-yl)-phenyl]urea | 3.1 | Active |
| N,N,N'—Trimethyl-N'—[3-(3-methyl-1,2,4-triazolo[4,3-b]pyridazin-6-yl)-phenyl]urea | 25 | Active |
| N—Methyl-N—[3-(1,2,4-triazolo[4,3-b]-pyridazin-6-yl)phenyl]acetamide | 12.5 | Active |
| N—Ethyl-N—[3-(1,2,4-triazolo[4,3-b]-pyridazin-6-yl)phenyl]acetamide | 12.5 | Active |
| N—Methyl-N—[3-(1,2,4-triazolo[4,3-b]-pyridazin-6-yl)phenyl]propanamide | 25 | Active |
| N—Ethyl-N—[3-(1,2,4-triazolo[4,3-b]-pyridazin-6-yl)phenyl]propanamide | 3.1 | Active |
| Ethyl-[3-(1,2,4-triazolo[4,3-b]-pyridazin-6-yl)phenyl]carbamic acid, methyl ester | 25 | Active |
| N—[3-(3-Methyl-1,2,4-triazolo[4,3-b]-pyridazin-6-yl)phenyl]-N—2-propenyl-acetamide | 25 | Active |
| N—(Cyclopropylmethyl)-N—[3-(3-methyl-1,2,4-triazolo[4,3-b]pyridazin-6-yl)-phenyl]acetamide | 6.2 | Active |
| N—[3-(3-Methyl-1,2,4-triazolo[4,3-b]-pyridazin-6-yl)phenyl]-N—2-propynyl-acetamide | 1.5 | Active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, pg 732 (April, 1977) and H. Mohler, et al., Science, 198, pg 849 (1977) was employed.

Male albino rats (Wistar strain, weighing 150–200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen (−20° C.) until time of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3$H-diazepam (1.5 nM, final concentration) or $^3$H-flunitrazepam (1.0 nM, final concentration) which was added to 1.5 ml of 50 mM Tris.HCl (pH 7.4). Non-specific binding controls and total binding controls received 100 μl of diazepam (3 μM final concentration) and 100 μl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials.

After drying at 50°-60° C. for 30 minutes, 10 ml of Beckman Ready-Solve HP was added and the radioactivity determined in a Beckman Scintillation Counter.

Inhibition of binding was calculated by the difference between total binding and binding in the presence of test compound, divided by the total binding, ×100.

The results of this test on representative compounds of this invention appear in Table III.

TABLE III

Inhibition of the Binding of $^3$H—Benzodiazepine to Brain-Specific Receptors of Rats

| Compound | % Inhibition |
|---|---|
| N—Ethyl-N—[3-(3-methyl-1,2,4-triazolo[4,3-b]pyridazin-6-yl)phenyl]acetamide | 90 |
| N—[3-(3-Methyl-1,2,4-triazolo[4,3-b]pyridazin-6-yl)phenyl]propanamide | 56 |
| N—Methyl-N—[3-(3-methyl-1,2,4-triazolo[4,3-b]pyridazin-6-yl)phenyl]propanamide | 89 |
| N—Ethyl-N—[3-(3-methyl-1,2,4-triazolo[4,3-b]pyridazin-6-yl)phenyl]propanamide | 95 |
| Ethyl[3-(3-methyl-1,2,4-triazolo[4,3,-b]pyridazin-6-yl)phenyl]carbamic acid, methyl ester | 60 |
| [3-(3-Methyl-1,2,4-triazolo[4,3-b]pyridazin-6-yl)phenyl]carbamic acid, methyl ester | 18 |
| Methyl[3-(3-methyl-1,2,4-triazolo[4,3-b]pyridazin-6-yl)phenyl]carbamic acid, methyl ester | 62 |
| N,N—Dimethyl-N'—[3-(3-methyl-1,2,4-triazolo[4,3-b]pyridazin-6-yl)phenyl]urea | 10 |
| N—Ethyl-N'N'—dimethyl-N—[(3-methyl-1,2,4-triazolo[4,3-b]pyridazin-6-yl)phenyl]urea | 66 |
| N—Methyl-N—[3-(1,2,4-triazolo[4,3-b]pyridazin-6-yl)phenyl]acetamide | 45 |
| N—Ethyl-N—[3-(1,2,4-triazolo[4,3-b]pyridazin-6-yl)phenyl]acetamide | 78 |
| N—[3-(3-Methyl-1,2,4-triazolo[4,3-b]pyridazin-6-yl)phenyl]-N—propylacetamide | 93 |
| N—Methyl-N—[3-(1,2,4-triazolo[4,3-b]pyridazin-6-yl)phenyl]propanamide | 56 |
| N—Ethyl-N—[3-(1,2,4-triazolo[4,3-b]pyridazin-6-yl)phenyl]propanamide | 84 |
| [3-(1,2,4-Triazolo[4,3-b]pyridazin-6-yl)phenyl]carbamic acid, methyl ester | 18 |
| Ethyl[3-(1,2,4-triazolo[4,3-b]pyridazin-6-yl)phenyl]carbamic acid, methyl ester | 78 |
| Methyl[3-(1,2,4-triazolo[4,3-b]pyridazin-6-yl)phenyl]carbamic acid, methyl ester | 62 |
| N—[3-(3-Methyl-1,2,4-triazolo[4,3-b]pyridazin-6-yl)phenyl]-N—2-propenylacetamide | 96 |
| N—(Cyclopropylmethyl)-N—[3-(3-methyl-1,2,4-triazolo[4,3-b]pyridazin-6-yl)phenyl]acetamide | 93 |
| N—2-Propynyl-N—[3-(1,2,4-triazolo[4,3-b]pyridazin-6-yl)phenyl]acetamide | 49 |
| N—2-Propenyl-N—[3-(1,2,4-triazolo[4,3-b]pyridazin-6-yl)phenyl]acetamide | 68 |
| N—[3-(3-Amino-1,2,4-triazolo[4,3-b]pridazin-6-yl)phenyl]-N—methylacetamide | 58 |
| N—[3-(3-Amino-1,2,4-triazolo[4,3-b]pridazin-6-yl)phenyl]-N—ethylacetamide | 90 |
| N—Methyl-N—[3-(3-methyl-1,2,4-triazolo[4,3-b]pridazin-6-yl)phenyl]-acetamide | 89 |
| N—[3-(3-Methyl-1,2,4-triazolo[4,3-b]pridazin-6-yl)phenyl]-N—2-propynylacetamide | 90 |

The novel compounds of the present invention have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenylalpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain one or more of the following: A binder such as gum tragacanth, acacia, corn starch or gelatin; excipients such as dicalcium phosphate; a disintegrating agent such as corn starch, potato starch, alginic acid and the like; a lubricant such as magnesium stearate; a wetting agent such as sodium lauryl sulfate and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such a cherry or orange flavor. Of course, any material used in preparing any dosage unit form should be pharmaceutically pure and substantially nontoxic in the amounts employed.

The following non-limiting examples illustrate the preparation of representative compounds of the presentation.

EXAMPLE 1

N-Ethyl-N-[3-(3-methyl-1,2,4-triazolo[4,3-b]pyridazin-6-yl)phenyl]acetamide

To 12.5 g of N-[3-(3-methyl-1,2,4-triazolo[4,3-b]pyridazin-6-yl)phenyl]acetamide (U.S. Pat. No. 4,112,095) in 500 ml of dimethylformamide under argon, was added 2.47 g of sodium hydride (50% in oil). The mixture was stirred for one hour, then 4.1 ml of ethyl iodide was added. This mixture was stirred for 2.5 days, then poured into 1.5 liters of water and extracted with 150 ml portions of dichloromethane. The extracts were combined, dried and evaporated in vacuo. The residue was chromatographed on a Waters Prep 500 silica gel column, eluting with dichloromethane:methanol (97:3). Fractions 8–13 were combined, evaporated in vacuo and the solid recrystallized from dichloromethane-hexane, giving 6.54 g of the desired product, mp 180°–185° C.

EXAMPLE 2

N-Methyl-N-[3-(3-methyl-1,2,4-triazolo[4,3-b]pyridazin-6-yl)phenyl]acetamide

A 12.5 g portion of N-[3-(3-methyl-1,2,4-triazolo[4,3-b]pyridazin-6-yl)phenyl]acetamide was added to 500 ml of dimethylformamide under argon. A 2.47 g portion of sodium hydride (50% in oil) was added, this mixture was stirred one hour, then 3.2 ml of methyl iodide was added. This mixture was stirred for 2.5 days, then poured into 1.5 liters of water and extracted with 150 ml portions of dichloromethane. The extracts were combined, dried and concentrated in vacuo. The residue was chromatographed as described in Example 1. Fractions 8–15 were combined, concentrated and the solid recrystallized from dichloromethane-hexane, giving 8.5 g of the desired product, mp 200°–203° C.

EXAMPLE 3

N-[3-(3-Methyl-1,2,4-triazolo[4,3-b]pyridazin-6-yl)phenyl]propanamide

A mixture of 7.38 g of 3-methyl-6-[3-(amino)phenyl]-1,2,4-triazolo[4,3-b]pyridazine and 50 ml of propionic anhydride was heated on a steam bath for one hour and then stirred at room temperature for 3 hours. The mixture was then diluted with 50 ml of ether, the solid was collected, washed with ether and recrystallized by dissolving in 150 ml of dichloromethane containing 10 ml of ethanol while heating and adding hexane until crystals appeared. Chilling produced crystals which were collected, giving 8.42 g of the desired product as tan crystals, mp 265°–268° C.

EXAMPLE 4

N-Methyl-N-[3-(3-methyl-1,2,4-triazolo[4,3-b]pyridazin-6-yl)phenyl]propanamide

A mixture of 2.52 g of N-[3-(3-methyl-1,2,4-triazolo[4,3-b]pyridazin-6-yl)phenyl]propanamide, 100 ml of dimethylformamide and 0.43 g of sodium hydride (60% in oil) was stirred at room temperature. A 1.53 g portion of methyl iodide in 10 ml of dimethylformamide was added and the procedure of Example 1 was followed, giving 1.15 g of the desired product, mp 150°–152° C.

EXAMPLE 5

N-Ethyl-N-[3-(3-methyl-1,2,4-triazolo[4,3-b]pyridazin-6-yl)phenyl]propanamide

To 6.1 g of N-[3-(3-methyl-1,2,4-triazolo[4,3-b]pyridazin-6-yl)phenyl]propanamide in 200 ml of dry dimethylformamide under argon, was added 1.1 g of sodium hydride (50% in oil). The mixture was stirred for one hour, then 1.86 ml of ethyl iodide was added. This mixture was stirred overnight and then treated as described in Example 1. The chromatography fractions containing the product were combined and the solid recrystallized as described in Example 1, giving 4.37 g of the desired product, mp 145°–148° C.

EXAMPLE 6

N-[3-(3-Methyl-1,2,4-triazolo[4,3-b]pyridazin-6-yl)phenyl]-N-propylacetamide

To 10.0 g of N-[3-(3-methyl-1,2,4-triazolo[4,3-b]pyridazin-6-yl)phenyl]acetamide in 500 ml of dry dimethylformamide under argon, was added 2.0 g of sodium hydride (50% in oil). This mixture was stirred for 1 hour, then 3.75 ml of 3-bromopropane was added. This mixture was stirred for 2.5 days, then poured into 1 liter of water and extracted with 150 ml portions of dichloromethane. The extracts were combined, dried and evaporated in vacuo. The residue was chromatographed as described in Example 1, giving 3.60 g of the desired product as yellow crystals, mp 145°–149° C.

EXAMPLE 7

N-[3-(3-Methyl-1,2,4-triazolo[4,3-b]pyridazin-6-yl)phenyl]-N-2-propenylacetamide To 3.0 g of N-[3-(3-methyl-1,2,4-triazolo[4,3-b]pyridazin-6-yl)phenyl]acetamide in 250 ml of dimethylformamide under argon, was added 0.6 g of sodium hydride (50% in oil). This mixture was stirred for 1 hour, then 1.07 ml of allyl bromide was added. The mixture was stirred overnight, then poured into 200 ml of water and extracted with 150 ml portions of dichloromethane. The extracts were combined, dried and evaporated in vacuo. The residue was chromatographed as described in Example 1. The active fractions were combined, evaporated and the solid recrystallized from ethyl acetate-hexane, giving 1.46 g of the desired product as tan crystals, mp 114°–115° C.

EXAMPLE 8

N-(Cyclopropylmethyl)-N-[3-(3-methyl-1,2,4-triazolo[4,3-b]pyridazin-6-yl)phenyl]acetamide A mixture of 3.0 g of N-[3-(3-methyl-1,2,4-triazolo[4,3-b]pyridazin-6-yl)phenyl]acetamide, 0.6 g of sodium hydride (50% in oil) and 250 ml of dimethylformamide was stirred under argon for 1 hour, then 1.2 ml of (bromomethyl)cyclopropane was added. This mixture was stirred overnight, then poured into 200 ml of water and extracted with 150 ml portions of dichloromethane. The extracts were combined, dried and evaporated. The residue was chromatographed on a silica gel column, eluting with dichloromethane:methanol (95:5). The active fractions were combined, evaporated and the solid recrystallized from ethyl acetate-hexane, giving 1.5 g of the desired product as pink crystals, mp 118°–121° C.

EXAMPLE 9

N-Methyl-N-[3-(1,2,4-triazolo[4,3-b]pyridazin-6-yl)phenyl]acetamide

To 2.53 g of N-[3-(1,2,4-triazolo[4,3-b]pyridazin-6-yl)phenyl]acetamide in 100 ml of dry dimethylformamide was added 0.6 g of sodium hydride (50% in oil). This mixture was stirred under argon, for 1 hour, then 0.78 ml of methyl iodide was added. This mixture was stirred overnight, then poured into 300 ml of water and extracted with 50 ml portions of dichloromethane. The extracts were combined, dried and evaporated in vacuo. The residue was chromatographed on a silica gel column, eluting with dichloromethane:methanol (98:2). The active fractions were combined, evaporated and the solid recrystallized from dichloromethane-hexane, giving 1.39 g of the desired product as light orange crystals mp 166°–169° C.

EXAMPLE 10

N-Ethyl-N-[3-(1,2,4-triazolo[4,3-b]pyridazin-6-yl)phenyl]acetamide

A mixture of 1.82 g of N-[3-(1,2,4-triazolo[4,3-b]pyridazin-6-yl)phenyl]acetamide, 0.43 g of sodium hydride (50% in oil), 100 ml of dimethylformamide and 0.7 ml of ethyl iodide were reacted as described in Example 9, giving 1.20 g of the desired product as tan crystals mp 122°–127° C.

EXAMPLE 11

N-Methyl-N-[3-(1,2,4-triazolo[4,3-b]pyridazin-6-yl)phenyl]propanamide

A mixture of 3.58 g of N-[3-(1,2,4-triazolo[4,3-b]pyridazin-6-yl)phenyl]propanamide, 0.71 g of sodium hydride (50% in oil) and 200 ml of dimethylformamide was stirred under argon, for 1 hour. A 0.92 ml portion of methyl iodide was added and the mixture was stirred overnight. A 0.355 g portion of sodium hydride (50% in oil) and 0.46 ml of methyl iodide were added and stirring was continued overnight. The mixture was poured into 200 ml of water and extracted with 150 ml portions of dichloromethane. The extracts were combined, dried and evaporated in vacuo. The residue was crystallized from ethyl acetate-hexane, giving 1.60 g of the desired product as light orange crystals, mp 146°–150° C.

EXAMPLE 12

N-Ethyl-N-[3-(1,2,4-triazolo[4,3-b]pyridazin-6-yl)phenyl]propanamide

The procedure of Example 11 was repeated using 1.17 ml of ethyl iodide in place of methyl iodide with supplemental addition of 0.585 ml of ethyl iodide. The residue from the dichloromethane extraction was chromatographed as described in Example 1, and recrystallized from ethyl acetate-hexane, giving 1.84 g of the desired product as yellow crystals, mp 127°–130° C.

EXAMPLE 13

N-2-Propynyl-N-[3-(1,2,4-triazolo[4,3-b]pyridazin-6-yl)phenyl]acetamide

A mixture of 3.0 g of N-[3-(1,2,4-triazolo[4,3-b]pyridazin-6-yl)phenyl]acetamide, 0.6 g of sodium hydride (50% in oil), 250 ml of dimethylformamide and 1.38 ml of propargyl bromide was reacted as described in Example 5, giving 1.77 g of the desired product as orange crystals, mp 195°–198° C.

EXAMPLE 14

N-2-Propenyl-N-[3-(1,2,4-triazolo[4,3-b]pyridazin-6-yl)phenyl]acetamide

The procedure of Example 13 was repeated using 1.07 ml of allyl bromide in place propargyl bromide, giving 1.96 g of the desired product as yellow-orange crystals mp 139°–142° C.

EXAMPLE 15

[3-(1,2,4-Triazolo[4,3-b]pyridazin-6-yl)phenyl]carbamic acid, methyl ester

To a solution of 5.0 g of 6-[3-(aminophenyl]-1,2,4-triazolo[4,3-b]pyridazine in 1 liter of dichloromethane and 120 ml of methanol was added 4.5 ml of N,N-diisopropylethylamine followed by 2 ml of methyl chloroformate. This mixture was stirred for 2.5 hours, then poured into 200 ml of saturated aqueous sodium bicarbonate and extracted with 150 ml portions of dichloromethane. The extracts were combined and treated as described in Example 1. The solid was recrystallized from dichloromethane-methanol-hexane, giving 4.5 g of the desired product as tan crystals, mp 210°–212° C.

EXAMPLE 16

Methyl-[3-(1,2,4-triazolo[4,3-b]pyridazin 6-yl)phenyl]carbamic acid, methyl ester A mixture of 2.25 g of [3-(1,2,4-triazolo[4,3-b]pyridazin-6-yl)phenyl]carbamic acid, methyl ester, 0.42 g of sodium hydride (50% in oil) and 200 ml of dimethylformamide was stirred under argon, for 1 hour and then 0.55 ml of methyl iodide was added. This mixture was stirred overnight, then treated as described in Example 1, giving 1.3 g of the desired product as tan crystals, mp 195°–199° C.

EXAMPLE 17

Ethyl[3-(1,2,4-triazolo[4,3-b]pyridazin-6-yl)phenyl]carbamic acid, methyl ester

The procedure of Example 16 was repeated, using 0.7 ml of ethyl iodide in place of methyl iodide, giving 1.68 g of the desired product as tan crystals, mp 131°–135° C.

EXAMPLE 18

Ethyl[3-(3-methyl-1,2,4-triazolo[4,3-b]pyridazin-6-yl)phenyl]carbamic acid, methyl ester To a solution of 1.0 g of 3-methyl-6-[3-(amino)-phenyl]-1,2,4-triazolo[4,3-b]pyridazine in 200 ml of dichloromethane was added 0.36 ml of methyl chloroformate and 0.81 ml of diisopropylethylamine. The mixture was stirred for 3 hours and the solid collected, giving 0.9 g of [3-(3-methyl-1,2,4-triazolo[4,3-b]pyridazin-6-yl)phenyl]carbamic acid, methyl ester. A 0.8 g portion of this compound was suspended in 100 ml of dimethylformamide together with 0.15 g of hexane washed sodium hydride (50% in oil). After 30 minutes, 0.22 ml of ethyl iodide was added. This mixture was stirred 2 hours, then poured into saturated aqueous sodium bicarbonate and extracted with dichloromethane. The extracts were combined, dried and evaporated in vacuo. The residue in dichloromethane:methanol (95:5) was filtered through a short pad of silica gel and the filtration was concentrated. The resulting solid was recrystallized from dichloromethane-hexane, giving 0.32 g of the desired product as off-white crystals, mp 176°–178° C.

EXAMPLE 19

N,N-Dimethyl-N'-[3-(3-methyl-1,2,4-triazolo[4,3-b]pyridazin-6-yl)phenyl]urea

To a solution of 1.9 g of 3-methyl-6-[3-(amino)-phenyl]-1,2,4-triazolo[4,3-b]pyridazine and 1.6 ml of diisopropylethylamine in dichloromethane was added 1.67 g of trichloromethyl chloroformate. This mixture was stirred for 1 hour, then two equivalents of dimethylamine hydrochloride were used. Diisopropylethylamine was added until solution was complete then the mixture was stirred for 1 hour, poured into saturated aqueous sodium bicarbonate and extracted with dichloromethane. The extracts were combined, dried and the solvent removed. The residue was chromatographed on a 200 g silica gel column using dichloromethane:methanol (95:5) as eluent. The active fractions were combined, evaporated and the solid recrystallized from dichloromethane-methanol-hexane, giving 1.33 g of the desired product as pale yellow crystals, mp 237°–239° C.

EXAMPLE 20

[3-(3-Methyl-1,2,4-triazolo[4,3-b]pyridazin-6-yl)phenyl]carbamic acid, methyl ester To a solution of 9.24 g of 3-methyl-6-[3-(amino)-phenyl]-1,2,4-triazolo[4,3-b]pyridazine in 1.5 liters of dichloromethane was added 7.9 ml of N,N-diisopropylethylamine followed by 3.5 ml of methyl chloroformate. This mixture was stirred for 3 hours, then the solid was collected and washed with 100 ml of dichloromethane. The solid was heated with dichloromethane-hexane and filtered, giving 8.25 g of the desired product as crystals, mp 150°–153° C. (dec.).

EXAMPLE 21

N,N,N'-Trimethyl-N'-[3-(3-methyl-1,2,4-triazolo[4,3-b]pyridazin-6-yl)phenyl]urea A suspension of 1.0 g of N,N-dimethyl-N'-[3-(3-methyl-1,2,4-triazolo[4,3-b]pyridazin-6-yl)phenyl]urea and 0.09 g of sodium hydride in 100 ml of dry dimethylformamide was stirred for 30 minutes, then 0.23 ml of methyl iodide was added. This solution was stirred overnight, then poured into saturated aqueous sodium bicarbonate and extracted with four 100 ml portions of dichloromethane. The extracts were combined and treated as described in Example 19, giving 0.8 g of the desired product as off-white crystals mp 159°–161° C.

EXAMPLE 22

N-Ethyl-N',N'-dimethyl-N-[(3-methyl-1,2,4-triazolo[4,3-b]pyridazin-6-yl)phenyl]urea A suspension of 1.0 g of N,N-dimethyl-N'-[3-(3-methyl-1,2,4-triazolo[4,3-b]pyridazin-6-yl)phenyl]urea and 0.08 g of sodium hydride in 100 ml of dry dimethylformamide was stirred for 30 minutes, then 0.26 ml of ethyl iodide was added. This solution was stirred overnight, then poured into saturated aqueous sodium bicarbonate and extracted with 100 ml portions of dichloromethane. The extracts were combined and treated as described in Example 19, giving 1.1 g of the desired product as off-white crystals, mp 138°–140° C.

EXAMPLE 23

Methyl[3-(3-methyl-1,2,4-triazolo[4,3-b]-pyridazin-6-yl)phenyl]carbamic acid, methyl ester A mixture of 1.27 g of [3-(3-methyl-1,2,4-triazolo[4,3-b]pyridazin-6-yl)phenyl]carbamic acid, methyl ester, 100 ml of dry dimethylformamide and 0.129 g of sodium hydride was stirred under argon, for 30 minutes, then 0.31 ml of methyl iodide was added. This mixture was stirred for 2 hours, then poured into saturated aqueous sodium bicarbonate and extracted with dichloromethane. The extracts were combined, dried and evaporated. The residue was dissolved in dichloromethane:methanol (95:5) and filtered through a short plug of silica gel. The filtrate was concentrated and the resulting solid chromatographed on a column of 500 g of silica gel, eluting with dichloromethane:methanol (97:3). Fractions containing product were combined, evaporated and the solid recrystallized from dichloromethane-hexane, giving 0.92 g of the desired product as off-white crystals, mp 164°–166° C.

EXAMPLE 24

N-[3-(1,6-Dihydro-6-oxo-3-pyridazinyl)phenyl]acetamide

To a solution of 20.0 g of 6-(3-nitrophenyl)-3(2H)-pyridazinone in 100 ml of trifluoroacetic acid was added 0.1 g of 10% palladium on carbon. The mixture was hydrogenated in a Parr shaker for 5 hours under 20–40 lbs pressure of hydrogen. The mixture was filtered through diatomaceous earth and the filtrate concentrated in vacuo. To the residue was added saturated aqueous sodium bicarbonate and the solids were collected and washed with water giving 14.8 g of 6-(3-aminophenyl)-3(2H)-pyridazinone.

A 13.5 g portion of the above compound in 250 ml of acetic anhydride was heated at 100° C. for 6 hours, then chilled and filtered, giving 4.02 g of solid. The filtrate was concentrated in vacuo. To the residual red oil was added 40 ml of dichloromethane:methanol (9:1). Filtration and concentration of the mother liquors gave 12.2 g of solid. The solids were combined (16.22 g). An 8.0 g portion was dissolved in methanol containing 0.8 g of potassium hydroxide. After standing for 2.5 days the solution was neutralized with concentrated hydrochloric acid and the solid which separated was collected. This solid was recrystallized from dichloromethane-methanol, giving the desired compound as crystals, mp 250°–252° C. (dec.).

EXAMPLE 25

N-[3-(1,6-Dihydro-6-oxo-3-pyridazinyl)phenyl]acetamide

A mixture of 37 g of 6-(3-aminophenyl)-3(2H)-pyridazinone and 500 ml of acetic anhydride was heated at 85°–90° C. for 8 hours. The solvent was removed in vacuo and the residue dissolved in 500 ml of methanol. To this solution was added portionwise 40 g of potassium hydroxide. The solution was refluxed for 3 hours and the solvent removed in vacuo. The residue was dissolved in water and the solution neutralized with hydrochloric acid. The resulting solid was collected and recrystallized from dichloromethane-methanol, giving 10.8 g of the desired compound as crystals, mp 250°–252° C. (dec.).

EXAMPLE 26

N-[3-(6-Chloro-3-pyridazinyl)phenyl]acetamide

A solution of 4.0 g of N-[3-(1,6-dihydro-6-oxo-3-pyridazinyl)phenyl]acetamide in 100 ml of phosphorus oxychloride was heated at 55°–65° C. for 1.5 hours and then the excess phosphorus oxychloride was removed in vacuo. The residue was dissolved in dichloromethane and the solution poured onto 200 g of crushed ice. After stirring for 30 minutes the acidic mixture was neutralized with aqueous sodium bicarbonate. The mixture was filtered, giving 0.8 g of solid. The dichloromethane layer of the filtrate was separated, dried and evaporated, giving 2.93 g of solid. The two solids were combined (3.73 g) and a 2.9 g portion chromatographed on a silica gel column, eluting with dichloromethane-methanol (95:5). The fractions containing product were combined, evaporated and the solid (1.5 g) recrystallized from dichloromethane-acetone, to give the desired compound as tan crystals, mp 203°–205° C. (dec.).

EXAMPLE 27

N-Methyl-N-[3-(6-chloro-3-pyridazinyl)phenyl]acetamide

A mixture of 2.25 g of N-[3-(6-chloro-3-pyridazinyl)phenyl]acetamide, 0.48 g of sodium hydride (50% in oil) and 100 ml of dimethylformamide was stirred under argon for 1 hour. To the mixture was added 0.6 ml of methyl iodide and after stirring 5 hours, an additional 0.6 ml of methyl iodide. After stirring overnight, 0.3 g of sodium hydride (50% in oil), then 0.6 ml of methyl iodide were added and stirring continued for 2 hours. The mixture was poured into water, filtered and the filtrate extracted with 60 ml portions of dichloromethane. The extracts were combined, evaporated in vacuo and the residue triturated with hexane. The resulting solid was chromatographed as described in Example 26 to give 1.45 g of product which was recrystallized from dichloromethane-ether to give the desired compound as crystals, mp 118°–120° C.

EXAMPLE 28

N-[3-(1,6-Dihydro-6-oxo-3-pyridazinyl)phenyl]-propanamide

A mixture of 7.8 g of 6-(3-aminophenyl)-3(2H)-pyridazinone and 45 ml of propionic anhydride was heated at 105°–110° C. for 4.5 hours. After standing overnight the excess propionic anhydride was removed in vacuo. The residue was dissolved in 50 ml of methanol and 12 g of potassium hydroxide added portionwise. This solution was refluxed for 1.5 hours, then the solvent was removed in vacuo. The residue was dissolved in cold water and the solution neutralized with concentrated hydrochloric acid. The solid was collected and washed with water and ether. A 1.5 g portion was crystallized from dichloromethane:methanol (95:5) and then chromatographed on a silica gel column, eluting with dichloromethane:methanol (95:5), giving the desired compound as white crystals, mp 229°–230° C.

EXAMPLE 29

N-[3-(6-chloro-3-pyridazinyl)phenyl]propanamide

To a refluxing solution of 0.63 g of N-[3-(1,6-dihydro-6-oxo-3-pyridazinyl)phenyl]propanamide in 100 ml of dry tetrahydrofuran was added 0.5 ml of phosphorus oxychloride. After 1.5 hours, 0.5 ml of phosphorus oxychloride was added and after 2 hours of refluxing 0.25 ml of phosphorus oxychloride was added. The solution was refluxed for an additional hour, then the solvent was removed, dichloromethane was added and the solution was poured into ice water. The mixture was neutralized with sodium bicarbonate and extracted with dichloromethane. The extracts were combined, washed with water, dried and the solvent removed giving an oil. This oil was chromatographed on thick layer silica gel preparative plates with dichloromethane:methanol (95:5), as solvent to give 0.33 g of solid. Recrystallization of 0.15 g from dichloromethane-acetone-hexane gave the desired compound as white crystals, mp 188°–189° C.

EXAMPLE 30

N-Methyl-N-[3-(3-amino-1,2,4-triazolo[4,3-b]pyridazin-6-yl)phenyl]acetamide

A solution of 2.2 g of N-methyl-N-[3-(6-chloro-3-pyridazinyl)phenyl]acetamide and 1.5 g of thiosemicarbazide in 100 ml of ethanol was refluxed for 5 hours, then the solvent was removed in vacuo. To the residue was added 100 ml of glacial acetic acid, this mixture was refluxed 18 hours, then the acetic acid was removed in vacuo. Saturated aqueous sodium bicarbonate was added to neutralize the mixture which was then extracted with dichloromethane:methanol (9:1). The extract was washed with water, dried and evaporated. The residue was chromatographed on a silica gel column, eluting with dichloromethane:methanol (9:1). The product was crystallized from dichloromethane-hexane, giving 0.6 g of the desired compound as yellow crystals mp 196°–197° C.

EXAMPLE 31

N-Ethyl-N-[3-(6-chloro-3-pyridazinyl)phenyl]acetamide

A mixture of 4.0 g of N-[3-(6-chloro-3-pyridazinyl)phenyl]acetamide, 0.85 g of sodium hydride (50% in oil) and 300 ml of dry dimethylformamide, under argon, was stirred for 1 hour then 1.42 ml of ethyl iodide was added. After stirring for 2.5 hours, 0.5 equivalent of sodium hydride and 1.1 equivalent of ethyl iodide were added. This mixture was stirred overnight, poured into 1 liter of water and extracted with five 100 ml portions of dichloromethane. The extracts were combined, dried and evaporated in vacuo, giving 3.6 g of the desired compound as tan crystals, mp 105°-110° C.

EXAMPLE 32

N-Ethyl-N-[3-(3-amino-1,2,4-triazolo[4,3-b]pyridazin-6-yl)phenyl]acetamide

A solution of 2.0 g of N-ethyl-N-[3-(6-chloro-3-pyridazinyl)phenyl]acetamide and 1.32 g of thiosemicarbazide in 100 ml of ethanol was refluxed for 8 hours, then evaporated in vacuo. To the residue was added 100 ml of glacial acetic acid. This mixture was refluxed overnight, then the solvent was removed in vacuo, 150 ml of water added and aqueous sodium bicarbonate added to neutralize the solution. This mixture was extracted with dichloromethane:methanol (9:1). The extracts were dried and evaporated. The residue was chromatographed on a silica gel column eluting with dichloromethane:methanol (9:1). The fractions containing product were combined and evaporated. The residue was chromatographed on silica gel thick layer preparative plates with dichloromethane:methanol (95:5) to give yellow crystals. Recrystallization from dichloromethane-ether-hexane gave 0.3 g of the desired compound as yellow crystals, mp 192°-193° C.

EXAMPLE 33

N-[3-(3-Methyl-1,2,4-triazolo[4,3-b]pyridazin-6-yl)phenyl]cyclobutanecarboxamide To a solution of 7.0 g of 3-methyl-6-(3-aminophenyl)-1,2,4-triazolo[4,3-b]pyridazine in 1.5 liters of dichloromethane was added 6 ml of N,N-diisopropylethylamine and 4.0 g of cyclobutane carboxylic acid chloride. This solution was stirred for 4 hours, washed with 200 ml of saturated aqueous sodium bicarbonate, dried and evaporated in vacuo. A small amount of dichloromethane was added and the mixture warmed to give 2.45 g of crystals. A second crop (3.5 g) was recovered from the mother liquor. Recrystallization from dichloromethane-hexane gave the desired compound as white crystals, mp 242°-245° C.

EXAMPLE 34

N-Ethyl-N-[3-(3-methyl-1,2,4-triazolo[4,3-b]pyridazin-6-yl)phenyl]cyclobutanecarboxamide A mixture of 2.0 g of N-[3-(3-methyl-1,2,4-triazolo[4,3-b]pyridazin-6-yl)phenyl]cyclobutanecarboxamide and 0.36 g of sodium hydride (50% in oil) in 200 ml of dry dimethylformamide, under argon, was stirred for 1 hour, then 0.6 ml of ethyl iodide was added. This mixture was stirred overnight, then poured into 200 ml of water and extracted with dichloromethane. The extracts were combined, dried and evaporated in vacuo. The residue was chromatographed on a silica gel column, eluting with dichloromethane:methanol (97:3). The fractions containing product were combined and evaporated, giving 0.81 g of the desired compound as yellow crystals, mp 157°-159° C.

EXAMPLE 35

N-Methyl-N-[3-(3-methyl-1,2,4-triazolo[4,3-b]pyridazin-6-yl)phenyl]cyclobutanecarboxamide The procedure of Example 34 was repeated using 0.47 ml of methyl iodide in place of ethyl iodide, giving after recrystallization from dichloromethane-hexane, 0.25 g of the desired compound as white crystals, mp 171°-173° C.

EXAMPLE 36

N-[3-(3-Methyl-1,2,4-triazolo[4,3-b]pyridazin-6-yl)phenyl]cyclopropanecarboxamide To a solution of 7.6 g of 3-methyl-6-(3-aminophenyl)-1,2,4-triazolo[4,3-b]pyridazine in 1.5 liters of dichloromethane was added 6 ml of N,N-diisopropylethylamine and 3.1 ml of cyclopropane carboxylic acid chloride. The solution was stirred at room temperature for 4 hours, washed with 200 ml of saturated sodium bicarbonate solution, dried and the solvent removed in vacuo. The residue was crystallized from dichloromethane-hexane to give 2.24 g of tan crystals, mp 255°-258° C. A sample recrystallized from dichloromethane-hexane gave white crystals, mp 259°-262° C.

EXAMPLE 17

N-Ethyl-N-[3-(3-methyl-1,2,4-triazolo[4,3-b]pyridazin-6-yl)phenyl]cyclopropanecarboxamide A mixture 1.57 g of N-[3-(3-methyl-1,2,4-triazolo[4,3-b]pyridazin-6-yl)phenyl]cyclopropanecarboxamide, 0.36 g of sodium hydride (50% in oil) and 200 ml of dry dimethylformamide under argon was stirred at room temperature for 1 hour and then 0.60 ml of ethyl iodide was added. After stirring overnight, the mixture was poured into 200 ml of water and extracted with dichloromethane. The combined extracts were dried, the solvent removed and the residue chromatographed on a silica gel column with dichlormethane-methanol (97:3) as solvent. The fractions containing product were combined, the solvent removed and the solid recrystallized from dichloromethane-hexane to give 0.80 g of pale yellow crystals, mp 149°-151° C.

EXAMPLE 38

N-Methyl-N-[3-(3-methyl-1,2,4-triazolo[4,3-b]pyridazin-6-yl)phenyl]cyclopropanecarboxamide The procedure of Example 37 was repeated using 0.47 ml of methyl iodide rather than ethyl iodide, giving 1.12 g of the desired compound as white crystals, mp 169°-172° C.

EXAMPLE 39

6-(3-Aminophenyl)-3-methyl-1,2,4-triazolo[4,3-b]pyridazine

An 11.0 g portion of 3-methyl-6-(3-nitrophenyl)-1,2,4-triazolo[4,3-b]pyridazine and 41.0 g portion of anhydrous stannous chloride were dissolved in 500 ml of anhydrous ethanol and heated to reflux for 3 hours. The solution was cooled to 20° C. and poured onto 200 g of crushed ice and 500 ml of dichloromethane. A saturated aqueous solution of sodium bicarbonate was added until pH=7. The mixture was filtered and the salts washed with five 100 ml portions of hot ethyl acetate. The organic layers were combined, dried over magnesium sulfate and the volatiles removed in vacuo. The residue was passed through a short column (50 g) of anhydrous magnesium silicate with dichloromethane-methanol (95:5) as eluent. The fractions containing product were collected, evaporated and recrystalized from dichloromethane-hexane to afford 8 g of the desired compound as yellow needles, mp 206°-208° C.

EXAMPLE 40

6-(3-Aminophenyl)-3-methyl-1,2,4-triazolo[4,3-b]pyridazine

A 103.0 g portion of 3-methyl-6-(3-nitrophenyl-1,2,4-triazolo[4,3-b]pyridazine and 1.0 g of 10% palladium on carbon were suspended in 2 liters of ethanol. The mixture was heated to reflux and 140 ml of anhydrous hydrazine added via a syringe pump over 24 hours. The solution was cooled to 20° C., filtered and the filtrate concentrated in vacuo. The residue was dissolved in 3 liters of hot dichloromethane and passed through a short column (200 g) of hydrous magnesium silicate with dichloromethane as the eluent. The fractions containing product were combined and evaporated, giving 83 g of the desired compound as yellow needles, mp 206°-208° C.

EXAMPLE 41

N-[3-(3-Methyl-1,2,4-triazolo[4,3-b]pyridazin-6-yl)phenyl]-N-2-propynylacetamide To 3.0 g of N-[3-(3-methyl-1,2,4-triazolo[4,3-b]pyridazin-6-yl)phenyl]acetamide in 250 ml of dimethylformamide under argon was added 0.6 g of sodium hydride (50% in oil). The mixture was stirred for one hour, then 1.38 ml of propargyl bromide was added. This mixture was stirred for 12 hours then poured into 200 ml of water and extracted with 150 ml portions of dichloromethane. The extracts were combined, dried and evaporated in vacuo. The residue was chromatographed on 300 g of silica gel with dichloromethane-methanol (97:3) as the eluent. Fractions containing the desired product were collected, evaporated in vacuo and recrystallized from dichloromethan-hexane to give 2.5 g of orange crystals mp 195°-198° C.

EXAMPLE 42

2,2-Dimethyl-N-[3-(3-methyl-1,2,4-triazolo[4,3-b]pyridazin-6-yl)phenyl]-propanamide To solution of 8.0 g of 3-methyl-6-[3-(amino)phenyl]-1,2,4-triazolo[4,3-b]pyridazine in 1.5 liters of dichloromethane was added 4.6 ml of trimethylacetyl chloride and 6.8 ml of diisopropylethylamine. The mixture was stirred for 3 hours and then poured into 200 ml of aqueous saturated sodium bicarbonate. The organic layer was separated, dried, and the solvent was removed in vacuo. The residue was recrystallized from dichloromethane-hexane to give 9.2 g of white crystals, mp 256°-258° C.

EXAMPLE 43

-N-2,2-Trimethyl-N-[3-(3-methyl-1,2,4-triazolo[4,3,b-]pyridazin-6-yl)phenyl]propanamide A 4.0 portion of 2,2-dimethyl-N-[3-(3-methyl-1,2,4-triazolo[4,3-b]pyridazin-6-yl)phenyl]propanamide was added to 500 ml of dimethylforamide under argon. A 6.74 g portion of sodium hydride (50% in oil) was added, this mixture stirred for one hour, then 1.0 ml of methyl iodide was added. This mixture was stirred for four (4) hours, then poured onto 500 ml of water and extracted with 150 ml portions of dichloromethane. The extracts were combined, dried and concentrated in vacuo. The residue was chromatographed on on a column of 300 g of silica gel with dichloromethane-methanol (97:3). Fractions containing the desired product were combined, evaporated in vacuo and the solid recrystalized from dichloromethane-hexane to give 2.5 g of white crystals, mp 178°-181° C.

EXAMPLE 44

N-Ethyl-2,2-dimethyl-N-[3-(3-methyl-1,2,4,-triazolo[4,3-b]-pyridazin-6-yl)phenyl]propanamide The procedure of Example 43 was repeated using 1.2 ml of ethyl iodide in place of methyl iodide. The residue from the dichloromethane extraction was chromatographed as described in Example 43, and then recrystalized from dichloromethane-hexane to give 1.85 g of the desired product as white crystals, mp 168°-170° C.

EXAMPLE 45

[3-(3-Methyl-1,2,4-triazolo[4,3-b]-pyridazin-6-yl)phenyl]carbamic acid, ethyl ester To a solution of 10.0 g of 3-methyl-6-[3-(amino)-phenyl]-1,2,4-triazolo[4,3-b]pyridazine in 1.5 liter of dichloromethane was added 4.7 ml of ethyl chloroformate and 8.9 ml of diisopropylethylamine. The mixture was stirred for 3 hours at room temperature, concentrated in vacuo to a volume of 500 ml, filtered and the solid washed with 200 ml of dichloromethane to give a tan powder, 11.4 g, mp 232°-235° C.

EXAMPLE 46

Methyl[3-(3-methyl-1,2,4-triazolo[4,3-b]pyridazin-6-yl)phenyl]carbamic acid, ethyl ester A mixture of 1.5 g of [3-(3-methyl-1,2,4-triazolo[4,3-b]-pyridazin-6-yl)phenyl]carbamic acid, ethyl ester, 0.29 g of sodium hydride (50% in oil) and 150 ml of dimethylformamide was stirred under argon for 1 hour and then 0.38 ml methyl iodide was added. This mixture was stirred overnight then poured onto 500 ml of water and extracted with 150 ml portions of dichloromethane. The extracts were combined, dried and concentrated in vacuo. The residue was chromatographed on 300 g of silica gel with dichloromethane-methanol (97:3). The fractions containing product were combined, the solvent evaporated in vacuo and the solid recrystalized from dichloromethane-hexane, to give 1.25 g of an off-white powder, mp 146°-149° C.

EXAMPLE 47

Ethyl[3-(3-methyl-1,2,4-triazolo[4,3-b]pyridazin-6-yl)phenyl]carbamic acid, ethyl ester The procedure of Example 46 was repeated using 0.48 ml of ethyl iodide in place of methyl iodide. The residue from the dichloromethane extraction was chromatographed as described in example 46, and then recrystalized from dichloromethane-hexane to give 1.3 g of white crystals, mp 132°-135° C.

EXAMPLE 48

N-Methyl-3-(3-methyl-1,2,4-triazolo-[4,3-b]pyridazin-6-yl)benzenamine

A mixture of 13.5 g of N-methyl-N-[3-(3-methyl-1,2,4-triazolo[4,3-b]-pyridazin-6-yl)phenyl]acetamide and 10 g of potassium hydroxide in 500 ml of ethanol was heated to reflux for 12 hours. The solution was concentrated in vacuo and the residue partitioned between 200 ml of brine and 300 ml of dichloromethane. The aqueous layer was extracted with 150 ml portions of dichloromethane. The combined organic layer and extracts were dried, concentrated in vacuo and the residue recrystalized from dichloromethane-hexane, to give 11.66 g of yellow crystals, mp 223°–226° C.

EXAMPLE 49

N-Methyl-N-[3-(3-methyl-1,2,4-triazolo-[4,3-b]pyridazin-6-yl)phenyl]-3-oxo-butanamide A mixture of 2.0 g of N-methyl-3-(3-methyl-1,2,4-triazolo-[4,3-b]pyridazin-6-yl)benzenamine and 2.14 ml of diketene in 250 ml of dry toluene was heated to reflux for 2 days. The solution was concentrated in vacuo and the residue partitioned between 300 ml dichloromethane and 200 ml of water. The aqueous layer was extracted with 150 ml portions of dichloromethane. The organic layer and extracts were combined, dried and concentrated in vacuo. The residue was chromatographed on 300 g of silica gel with dichloromethane-methanol (97:3). The fractions containing product were combined, evaporated in vacuo and the solid recrystalized from dichloromethane-hexane to give 1.15 g of tan crystals, mp 138°–141° C.

EXAMPLE 50

N-[3-(3-Methyl-1,2,4-triazolo-[4,3-b]pyridazin-6-yl)phenyl]formamide

To 5.53 ml of acetic-formic anhydride was added 250 ml dichloromethane followed by 10 g of 3-methyl-6-[3-(amino)-phenyl]-1,2,4-triazolo[4,3-b]pyridazine. The solution was stirred for 12 hours, then diluted with 1 liter of dichloromethane-methanol (9:1). This solution was washed with saturated aqueous sodium bicarbonate, dried, and concentrated in vacuo. The residue was recrystallized from dichloromethane-methanol to give 6.7 g of an off-white powder, mp 265°–268° C.

EXAMPLE 51

N-Methyl-N[3-(3-methyl-1,2,4-triazolo[4,3-b]pyridazin-6-yl)phenyl]formamide

A mixture of 2.5 g of N-[3-(3-methyl-1,2,4-triazolo-[4,3-b]-pyridazin-6-yl)phenyl]formamide, 0.56 g of sodium hydride (50% in oil) and 250 ml of dimethylformamide were reacted as described in example 2, giving 1.72 g of the desired product as a white powder, mp 207°–210° C.

EXAMPLE 52

N-Ethyl-N[3-(3-methyl-1,2,4-triazolo[4,3-b]pyridazin-6-yl)phenyl]formamide

The procedure of Example 51 was repeated using 0.92 ml of ethyl iodide in place of methyl iodide. The desired product was obtained as yellow crystals, 1.76 g. mp 156°–161° C.

EXAMPLE 53

1-[3-(3-Methyl-1,2,4-triazolo[4,3-b]pyridazin-6-yl)phenyl]-2-pyrolidinone

To a solution of 2 g of 3-methyl-6-[3-(amino)phenyl]-1,2,4-triazolo[4,3-b]pyridazine in 400 ml of dichloromethane was added 1.7 ml of diisopropylamine and 1 ml of 4-chlorobutyryl chloride. This solution was stirred for 12 hours, then poured onto 200 ml of saturated aqueous sodium bicarbonate and extracted with 150 ml portions of dichloromethane. The combined extracts were dried and concentrated in vacuo. The residue was dissolved in 200 ml of dimethylformamide and 2.0 g of potassium carbonate was added. This solution was heated to 80° C. for 12 hours, then poured onto 200 ml of water and extracted with 150 ml portions of dichloromethane. The combined extracts were dried, concentrated in vacuo and chromatographed on 300 g of silica gel with dichloromethane-methanol (97:3). The fractions containing the desired product were combined, concentrated in vacuo and the solid recrystalized from dichloromethane-hexane to give 1.67 g of white crystals, mp 235°–237° C.

EXAMPLE 54

1-[3-(3-Methyl-1,2,4-triazolo[4,3-b]-pyridazin-6-yl)phenyl]2-piperidone

The procedure of Example 53 was repeated using 1.26 ml of 5-chlorovaleryl chloride in place of 4-chlorobutyryl. The desired product was obtained as white crystals, 1.26 g, mp 204°–207° C.

EXAMPLE 55

N-(1-Methylethyl)-3-(3-methyl-1,2,4-triazolo[4,3-b]pyridazin-6-yl)benzenamine

To a solution of 5 g of 3-methyl-6-[3-(amino)phenyl]-1,2,4-triazolo[4,3-b]pyridizine and 2.5 ml of acetone in 250 ml methanol was added sufficient gaseous hydrochloric acid to bring the pH to 6. To this solution was added 2.5 g sodium cyanoborohydride. The solution was stirred for 12 hours with the pH maintained at 6 by periodic addition of hydrochloric acid. The solution was concentrated in vacuo, the residue poured onto saturated aqueous sodium bicarbonate and the solution extracted with 150 ml portions of dichloromethane. The combined extracts were concentrated in vacuo and chromatographed on 500 g of silica gel with dichloromethane-methanol (97:3). The fractions containing the desired product were combined, concentrated in vacuo and the solid recrystallized from dichloromethane-hexane to give 5.1 g of yellow crystals, mp 157°–159° C.

EXAMPLE 56

N-(1-Methylethyl)-3-(3-methyl-1,2,4-triazolo[4,3-b]pyridazin-6-yl)phenylacetamide To a solution of 2 g of N-(1-methylethyl)-3-(3-methyl-1,2,4-triazolo[4,3-b]pyridazin-6-yl)benzenamine and 1.43 ml diisopropylethylamine in 200 ml of dichloromethane was added 0.6 ml of acetylchloride. This solution was stirred for 12 hours, then poured onto 200 ml of water and extracted with 150 ml portions of dichloromethane. The combined extracts were dried, concentrated in vacuo and the solid chromatographed on 300 g of silica gel using dichloromethane-methanol (97:3). The fractions containing the desired product were combined, concentrated in vacuo and the solid recrystalized from dichloromethane-hexane to give 0.72 g of yellow crystals, mp 197°-200° C.

EXAMPLE 57

N-[3-(3-Methyl-1,2,4-triazolo[4,3-b]-pyridazin-6-yl)phenyl]butanamide

To a solution of 6 g of 3-methyl-6-[3-(amino)phenyl]-1,2,4-triazolo[4,3-b]pyridazine and 5.1 ml diisopropylethylamine in 500 ml dichloromethane was added 3.1 ml of butyryl chloride. This solution was stirred for 12 hours then poured onto 200 ml of water and extracted with 150 ml portions of dichloromethane. The combined extracts were dried, concentrated in vacuo and the solid chromatographed on 500 g silica gel with dichloromethane-methanol (95:5). The fractions containing the desired product were combined, concentrated in vacuo and the solid recrystallized from dichloromethane-hexane to give 5.58 g of white crystals, mp 195°-198° C.

EXAMPLE 58

N-Methyl-N-[3-(3-methyl-1,2,4-triazolo[4,3-b]pyridazin-6-yl)phenyl]butanamide

A mixture of 2 g of N-[3-(3-methyl-1,2,4-triazolo[4,3-b]-pyridazin-6-yl)phenyl]butanamide, 0.32 g sodium hydride (50% in oil), 0.41 ml of methyl iodide and 200 ml of dimethylformamide was reacted in the manner described in Example 2. The desired product was obtained as white crystals, 1.45 g, mp 140°-143° C.

EXAMPLE 59

N-Ethyl-N-[3-(3-methyl-1,2,4-triazolo[4,3-b]pyridazin-6-yl)phenyl]butanamide

The procedure of Example 58 was repeated using 0.53 ml of ethyl iodide in place of methyl iodide. The desired product was obtained as white crystals, 1.2 g, mp 127°-129° C.

EXAMPLE 60

3-(6-Chloro-3-pyridazinyl)benzenamine

A mixture of 50.0 g of 3-chloro-6-(3-nitrophenyl)-pyridazine, 160.8 g tin dichloride and 1000 ml ethanol was refluxed for 1.0 hr, then cooled and approximately ½ of the solvent removed by evaporation under reduced pressure. The reaction mixture was added to 2.5 liters saturated aqueous sodium bicarbonate solution. After adjusting the pH to ~8 with additional sodium bicarbonate, 1.2 liters of methylene chloride was added and stirring continued. The resulting mixture was filtered and the salts washed repeatedly with methylene chloride and ethyl acetate. All organic fractions were then combined, dried (MgSO₄) and the solvent removed in vacuo, to give 22 g of solid product, mp 118°-121° C.

The solids were suspended in methylene chloride (400 ml), stirred for 30 minutes and filtered to remove the insoluble side-product. Evaporation of solvent gave 20.1 g of product as yellow crystals, mp 120°-123° C.

EXAMPLE 61

N-[3-(6-Chloro-3-pyridazinyl)phenyl]acetamide

A solution of 34.0 g of 3-(6-chloro-3-pyridazinyl)benzenamine, 18.8 ml of acetic anhydride, 28.7 ml of diisopropylethylamine and 750 ml of dichloromethane was stirred for 2.5 hrs. The solution was concentrated in vacuo to half of the original volume and 200 ml of hexane was added. The solution was filtered, affording 26.4 g of tan solid. The filtrate was washed with saturated aqueous sodium bicarbonate, dried (Na₂SO₄) and concentrated in vacuo. The residue and the solid collected previously were combined and recrystallized from dichloromethane-acetone-hexane to give 35 g of tan crystals, mp 203°-205° C.

EXAMPLE 62

N-[3-(6-Chloro-3-pyridazinyl)phenyl]propionamide

A solution of 33.0 g of 3-(6-chloro-3-pyridazinyl)benzenamine, 25.0 g propionic anhydride and 20.7 diisopropylethylamine in 750 ml of dichloromethane was stirred for 3 hrs. The mixture was then treated as described in Example 61 to give 37.3 g of tan solids, mp 184°-187° C.

A small sample (1.5 g) was recrystalized from dichloromethane-methanol-hexane to give 1.1 g of colorless crystals, mp 188°-189° C.

EXAMPLE 63

N-Methyl-N[3-(6-chloro-3-pyridazinyl)phenyl]acetamide

To a solution of 3.0 g of sodium hydride (50% dispersion in oil) in 300 ml of anhydrous tetrahydrofuran under argon was added 14.0 g of N-[3-(6-chloro-3-pyridazinyl)phenyl]acetamide. The solution was stirred for 0.5 hours, then 3.9 ml of methyl iodide was added. After stirring for 2 hours, the solution was poured onto 400 ml of water and extracted with 100 ml portions of dichloromethane. The combined extracts were dried, concentrated in vacuo and chromatographed on hydrated magnesium silicate with dichloromethane-methanol (98:2) as eluant. The fractions containing the desired product were combined, concentrated in vacuo and recrystalized from acetone-hexane to give 14.1 g of cream crystals, mp 109°-112° C.

EXAMPLE 64

N-Ethyl-N[3-(6-chloro-3-pyridazinyl)phenyl]acetamide

To a solution of 4.0 g of sodium hydride (50% dispersion in oil) in 400 ml of anhydrous tetrahydrofuran was added 18.0 g of N-[3-(6-chloro-3-pyridazinyl)phenyl]acetamide. The solution was stirred for 0.5 hrs, then 6.4 ml ethyl iodide was added. After stirring for 18 hours, the reaction mixture was treated as described in Example 63 to give 19.8 g of colorless crystals, mp 116°-119° C. Recrystalization from acetone-hexane gave colorless crystals, mp 120°-121° C.

EXAMPLE 65

N-Methyl-N[3-(6-chloro-3-pyridazinyl)phenyl]-propanamide

To a solution of 3.6 g sodium hydride (50% dispersion in oil) in 800 ml anhydrous tetrahydrofuran was added 18.0 g of N-[3-(6-chloro-3-pyridazinyl]propanamide. The solution was stirred for 0.5 hour, then 4.7 ml methyl iodide was added. Stirring was continued for 2 hours and the reaction mixture was poured onto 800 ml water. Workup was carried out as described in Example 63 but without chromatographing. The dark oil product was refluxed in hexane and filtered to give 16.8 g of cream-colored solids, mp 104°-106° C. Recrystallization of 1.5 g afforded 1.10 g colorless flakes, mp 106°-107° C.

EXAMPLE 66

N-Ethyl-N-[3-(6-chloro-3-pyridazinyl)phenyl]propanamide

To a solution of 5.0 g sodium hydride (50% dispersion in oil) in 800 ml anhydrous tetrahydrofuran was added 17.0 g of N-[3-(6-chloro-3-pyridazinyl]propanamide. The solution was stirred for 0.5 hour, then 5.7 ml ethyl iodide was added. The reaction mixture was stirred for 18 hours, then poured into 800 ml water and treated as described in Example 61 to give 18.7 g of tan solid, mp 116°–118° C. Chromatography of 1.0 g of the crude product on silica gel with dichloromethane-methanol as solvent gave product which was recrystalized from acetone-hexane to afford colorless crystals, mp 118°–119° C.

EXAMPLE 67

N-Methyl-N-[3-(3-amino-1,2,4-triazolo[4,3-b]pyridazin-6-yl)phenyl]acetamide

A solution of 3.0 g N-methyl-N-[3-(6-chloro-3-pyridazinyl)phenyl]acetamide and 2.0 g thiosemicarbazide in 100 ml ethanol was heated at reflux for 5.5 hours. The ethanol was removed in vacuo, 100 ml glacial acetic acid added and the mixture was refluxed for 18 hours. The acetic acid was removed in vacuo and the yellow residue added to 300 ml water. This mixture was brought to pH ~7 with aqueous sodium bicarbonate and extracted with 100 ml portions of dichloromethane and dichloromethane-ethyl acetate. The combined extracts were dried, the solvent removed in vacuo, and the product mixture chromatographed on silica gel using dichloromethane-methanol (95.5) as solvent. Recombining the pure fractions and recrystalizing from ether-methanol-hexane afforded 1.10 g yellow crystals, mp 206°–207° C.

EXAMPLE 68

N-Methyl-N-[3-[3-(methylamino)-1,2,4-triazolo[4,3-b]pyridazin-6-yl]phenyl]acetamide A solution of 6.0 g N-methyl-N-[3-(6-chloro-3-pyridazinyl)phenyl]acetamide and 4.8 g 4-methylthiosemicarbazide in 200 ml ethanol was refluxed for 5 hours and treated in similar fashion to Example 67. Chromatography on silica gel with dichloromethane-methanol (96:4) and recrystalization from dichloromethane-hexane afforded 2.1 g yellow crystals, mp 213°–215° C.

EXAMPLE 69

N-Methyl-N-[3-[3-(ethylamino)-1,2,4-triazolo[4,3-b]pyridazin-6-yl]phenyl]acetamide A solution of 6.0 g N-methyl-N-[3-(6-chloro-3-pyridazinyl)phenyl]acetamide and 5.5 g 4-ethyl-3-thiosemicarbazide in 200 ml ethanol was refluxed for 18 hours and treated in similar fashion to Example 67. Chromatography on silica gel and recrystalization from dichloromethane-hexane afforded 1.2 g yellow crystals, mp 225°–227° C.

EXAMPLE 70

N-Ethyl-N[3-amino-1,2,4-triazolo[4,3-b]pyridazin-6-yl)phenyl]acetamide

A solution of 6.0 g N-ethyl-N-[3-(6-chloro-3-pyridazinyl)phenyl]acetamide and 4.0 g thiosemicarbazide in 200 ml ethanol was refluxed for 18 hours. The mixture was then further treated as described in Example 67. Chromatography by high pressure liquid chromatography on Waters-500 preparative apparatus (silica gel, dichloromethane-methanol 95:5) and recrystalization from dichloromethone-hexane afforded 2.5 g of yellow crystals, mp 207°–208° C.

EXAMPLE 71

N-Ethyl-N[3-[3-(methylamino)-1,2,4-triazolo[4,3-b]pyridazin-6-yl]phenyl]acetamide A solution of 7.0 g N-ethyl-N-[3-(6-chloro-3-pyridazinyl)phenyl]acetamide and 5.3 g 4-methyl thiosemicarbazide in 200 ml ethanol was refluxed for 18 hours. The mixture was worked up and the product chromatographed as described in Example 70. Recrystalization of the product fractions from dichloromethone-hexane afforded 2.1 g of yellow crystals, mp 193°–195° C.

EXAMPLE 72

N-Ethyl-N[3-[3-(ethylamino)-1,2,4-triazolo[4,3-b]pyridazin-6-yl]phenyl]acetamide A solution of 7.0 g N-ethyl-N-[3-(6-chloro-3-pyridazinyl)phenyl]acetamide and 6.0 g 4-ethyl-3-thiosemicarbazide in 200 ml ethanol was refluxed for 18 hours. The mixture was then worked up and the product chromatographed as described in Example 70. Recrystallization of the product from dichloromethane-hexane afforded 2.1 g yellow flakes, mp 171°–172° C.

EXAMPLE 73

N-Methyl-N-[3-(3-amino-1,2,4-triazolo[4,3-b]-pyridazin-6-yl)phenyl]propanamide

A solution of 6.0 g N-methyl-N-[3-(6-chloro-3-pyridazinyl)]propanamide and 4.0 g thiosemicarbazide in 200 ml ethanol was refluxed for 18 hours. The mixture was then treated and the product chromatographed as described in Example 70. Recrystalization of the product from dichloromethane-hexane afforded 2.4 g yellow powder, mp 190°–191° C.

EXAMPLE 74

N-Methyl-N-[3-[3-(methylamino)-1,2,4-triazolo[4,3-b]-pyridazin-6-yl]phenyl]propanamide A solution of 5.0 g of N-methyl-N-[3-(6-chloro-3-pyridazinyl)phenyl]propanamide and 3.8 g 4-methylthiosemicarbazide in 200 ml ethanol was refluxed for 18 hours. The mixture was then treated and the product chromatographed as described in Example 70. Recrystallization of the product from dichloromethane-hexane afforded 0.9 g yellow powder, mp 212°–213° C.

EXAMPLE 75

N-Methyl-N-[3-[3-(ethylamino)-1,2,4-triazolo[4,3-b]-pyridazin-6-yl]phenyl]propanamide A solution of 5.0 g N-methyl-N-[3-(6-chloro-3-pyridazinyl)phenyl]propanamide and 4.3 g 4-ethyl-3-thiosemicarbazide was refluxed for 18 hours. The mixture was then treated and the product chromatographed as described in Example 70. Recrystalization of the product from dichloromethane-hexane afforded 1.2 g of yellow crystals, mp 198°–199° C.

EXAMPLE 76

N-Ethyl-N-[3-(3-amino-1,2,4-triazolo[4,3-b]pyridazin-6-yl)phenyl]propanamide A solution of 5.0 g N-ethyl-N-[3-(6-chloro-3-pyridazinyl)phenyl]propanamide and 3.2 g thiosemicarbazide in 200 ml ethanol was refluxed for 18 hours. The mixture was treated and the product chromatographed as described for Example 70. Recrystalization of the product from dichloromethane-hexane afforded 2.4 g yellow crystals, mp 199°–200° C.

EXAMPLE 77

N-Ethyl-N-[3-[3-(methylamino)-1,2,4-triazolo[4,3-b]pyridazin-6-yl]phenyl]propanamide A solution of 5.0 g N-ethyl-N[3-(6-chloro-3-pyridazinyl)phenyl]propanamide and 3.8 g of 4-methylthiosemicarbazide in 200 ml ethanol was refluxed for 18 hours. The mixture was then treated and the product chromatographed as described for Example 70. Recrystallization of the product from acetone-hexane afforded 0.5 g orange crystals, mp 172°–173° C.

EXAMPLE 78

N-Ethyl-N-[3-[3-(ethylamino)-1,2,4-triazolo[4,3-b]-pyridazin-6-yl]phenyl]propanamide A solution of 5.5 g N-ethyl-N-[3-(6-chloro-3-pyridazinyl)phenyl]propanamide and 4.5 g 4-ethyl-3-thiosemicarbazide in 200 ml ethanol was refluxed for 18 hours. The mixture was treated and the product chromatographed as described for Example 70. Recrystallization of the product from acetone-hexane afforded 0.8 g yellow-orange crystals, mp 164°–166° C.

What is claimed:

1. A compound selected from those of the formula:

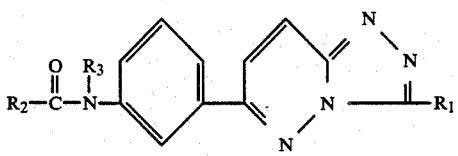

wherein $R_1$ is selected from the group consisting of hydrogen, alkyl($C_1$–$C_3$), amino, monoalkyl($C_1$–$C_3$)amino, dialkyl($C_1$–$C_3$)-amino, —NHCOalkyl($C_1$–$C_3$) and N-alkyl($C_1$–$C_3$)—CO-alkyl($C_1$–$C_3$); $R_2$ is selected from the group consisting of hydrogen, alkyl($C_1$–$C_6$), cycloalkyl($C_3$–$C_6$), —O-alkyl($C_1$–$C_6$), —NH-alkyl(-$C_1$–$C_3$), —N-dialkyl($C_1$–$C_3$), —($CH_2$)$_n$—O-alkyl(-$C_1$–$C_3$), —($CH_2$)$_n$—NH-alkyl($C_1$–$C_3$) and —($CH_2$)$_n$—N-dialkyl($C_1$–$C_3$), where n is an integer from 1 to 3 inclusive; and $R_3$ is selected from the group consisting of, alkyl($C_1$–$C_6$), alkenyl($C_2$–$C_6$), —$CH_2C\equiv CH$, cycloalkyl($C_3$–$C_6$)methyl, —$CH_2OCH_3$ and —$CH_2CH_2OCH_3$.

2. A compound according to claim 1, wherein $R_1$, is alkyl($C_1$–$C_3$), $R_2$ is alkyl($C_1$–$C_6$) and $R_3$ is alkyl($C_1$–$C_6$).

3. A compound according to claim 2, wherein $R_1$ is $CH_3$, $R_2$ is alkyl($C_1$–$C_3$) and $R_3$ is alkyl($C_1$–$C_2$).

4. A compound according to claim 3 which is selected from the group consisting of:
N-ethyl-N-[3-(3-methyl-1,2,4-triazolo[4,3-b]pyridazin-6-yl)phenyl]acetamide;
N-methyl-N-[3-(3-methyl-1,2,4-triazolo[4,3-b]pyridazin-6-yl)phenyl]acetamide;
N-methyl-N-[3-(3-methyl-1,2,4-triazolo[4,3-b]pyridazin-6-yl)phenyl]propanamide; and
N-ethyl-N-[3-(3-methyl-1,2,4-triazolo[4,3-b]pyridazin-6-yl)phenyl]propanamide.

5. The compound according to claim 1, ethyl[3-(3-methyl-1,2,4-triazolo[4,3-b]pyridazin-6-yl)phenyl]carbamic acid, methyl ester.

6. The compound according to claim 1, methyl[3-(3-methyl-1,2,4-triazolo[4,3-b]pyridazin-6-yl)phenyl]carbamic acid, methyl ester.

7. The compound according to claim 1, N-[3-(3-methyl-1,2,4-triazolo[4,3-b]pyridazin-6-yl)phenyl]-N-2-propynylacetamide.

8. The compound according to claim 1, N-[3-(3-methyl-1,2,4-triazolo[4,3-b]pyridazin-6-yl)phenyl]-N-2-propenylacetamide.

9. The compound according to claim 1, N-ethyl-N'N'-dimethyl-N-[(3-methyl-1,2,4-triazolo[4,3-b]pyridazin-6-yl)phenyl]urea.

10. The compound according to claim 1, N-ethyl-N-[3-(1,2,4-triazolo[4,3-b]pyridazin-6-yl)phenyl]propanamide.

11. The compound according to claim 1, N-methyl-N-[3-(3-methyl-1,2,4-triazolo[4,3-b]pyridazin-6-yl)phenyl]cyclopropanecarboxamide.

12. The compound according to claim 1, N-ethyl-N-[3-(3-methyl-1,2,4-triazolo[4,3-b]pyridazin-6-yl)phenyl]cyclopropanecarboxamide.

13. The compound according to claim 1, N-(cyclopropylmethyl)-N-[3-(3-methyl-1,2,4-triazolo[4,3-b]pyridazin-6-yl)phenyl]acetamide.

14. The compound according to claim 1, ethyl[3-(1,2,4-triazolo[4,3-b]pyridazin-6-yl)phenyl]carbamic acid, methyl ester.

15. A composition of matter in dosage unit form comprising from 2 to 750 mg of a compound of claim 1 in association with a pharmaceutically acceptable carrier.

* * * * *